United States Patent [19]
McClane

[11] Patent Number: 5,343,768
[45] Date of Patent: * Sep. 6, 1994

[54] SAMPLER FOR HOLDING SLIDES AND POLYMER SCRIMS OR PADS

[76] Inventor: M. Brent McClane, 3504 W. Main St., Belleville, Ill. 62223

[ * ] Notice: The portion of the term of this patent subsequent to Jun. 15, 2010 has been disclaimed.

[21] Appl. No.: 922,026

[22] Filed: Jul. 27, 1992

Related U.S. Application Data

[63] Continuation-in-part of Ser. No. 759,411, Sep. 13, 1991, Pat. No. 5,219,390.

[51] Int. Cl.$^5$ .............................................. G01N 1/10
[52] U.S. Cl. ..................................... 73/864; 206/456; 435/292
[58] Field of Search ...................... 73/864.91, 863, 864, 73/863.21, 863.31, 863.22, 170.29, 170.34, 863.23, 863.24, 863.25; 356/244, 36, 38; 435/292, 293, 284, 970; 359/391–398; 206/456, 455, 316.1, 557–565, 587, 589

[56] References Cited

U.S. PATENT DOCUMENTS 3,955,421 5/1976 Doernberg et al. ............... 73/864 X
4,308,028 12/1981 Elkins ............................... 73/864.72

OTHER PUBLICATIONS

Wildco Periphyton Sampler: *Wildco Sampling Equipment Catalog* No. 156, p. 53, published Feb. 1992.

Photographs of Periphyton Sampler; 3 views photographed by Feb. 1992.

*Primary Examiner*—Tom Noland
*Attorney, Agent, or Firm*—Armstrong, Teasdale, Schlafly & Davis

[57] ABSTRACT

A sampler device for supporting glass slides and/or polymer scrims or pads under water for the collection of plant and animal samples. The device comprises a frame having a top member, a bottom member, and left and right side members. The top and bottom members have a plurality of vertically aligned slots therein for receiving and holding the edges of a plurality of glass slides. The top and bottom members also have generally horizontally extending grooves for mounting a scrim or pad thereon. A guard is pivotally mounted to the frame, and movable between a closed position, in which portions of the guard overlap the ends of the slots in the top and bottom members of the frame, thereby securing the slides in the frame, and an open position in which the guard does not overlap the ends of the slots so that slides can be inserted into and removed from the slots. In the closed position the guard also overlaps the grooves to secure the scrim or pad therein. A lock is provided to retain the guard in its closed position. A mounting bolt extends through the top and bottom of the frame. Eyes on the mounting bolts permit lines to be attached to the bolts for securing the sampler device under water.

12 Claims, 4 Drawing Sheets

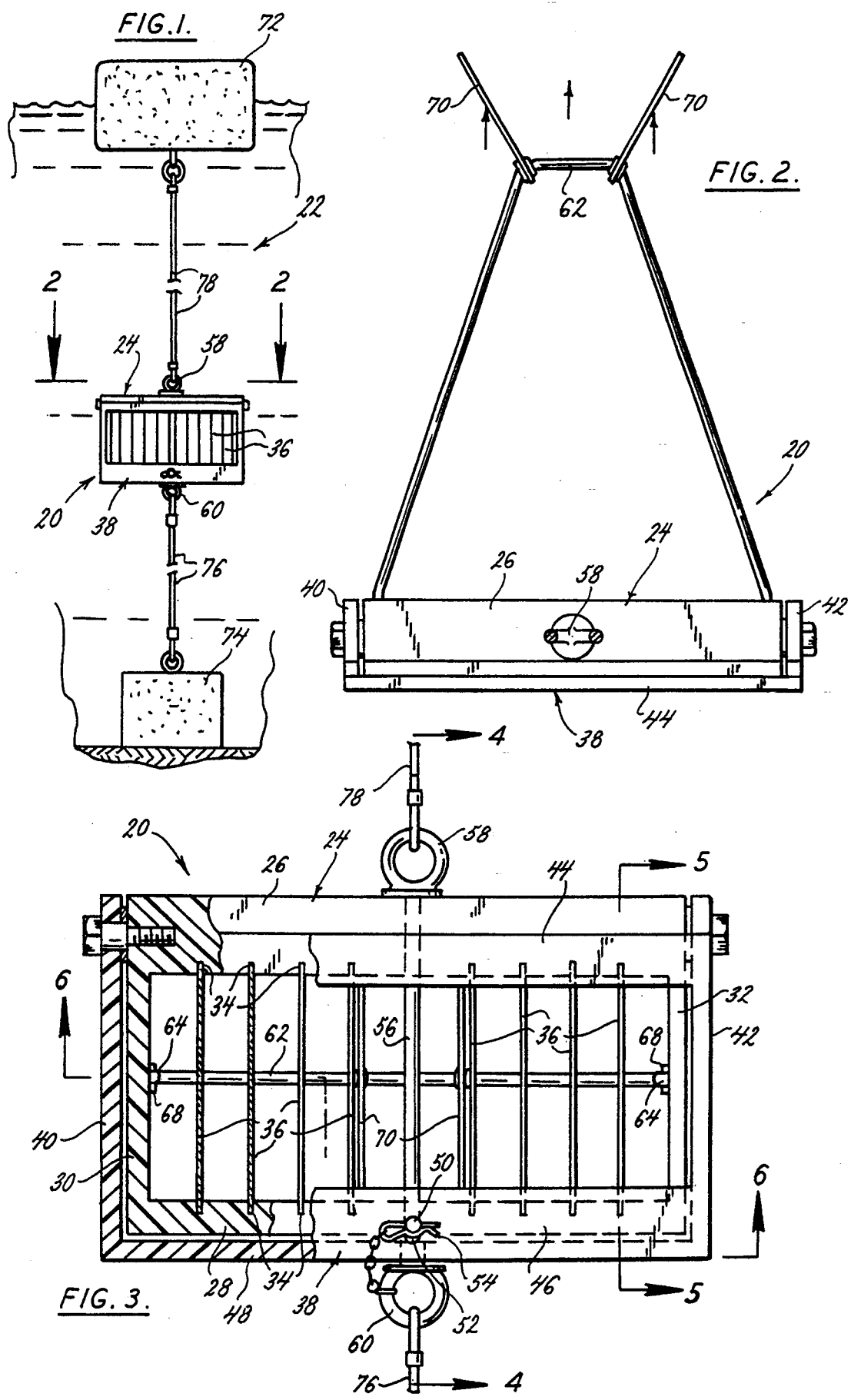

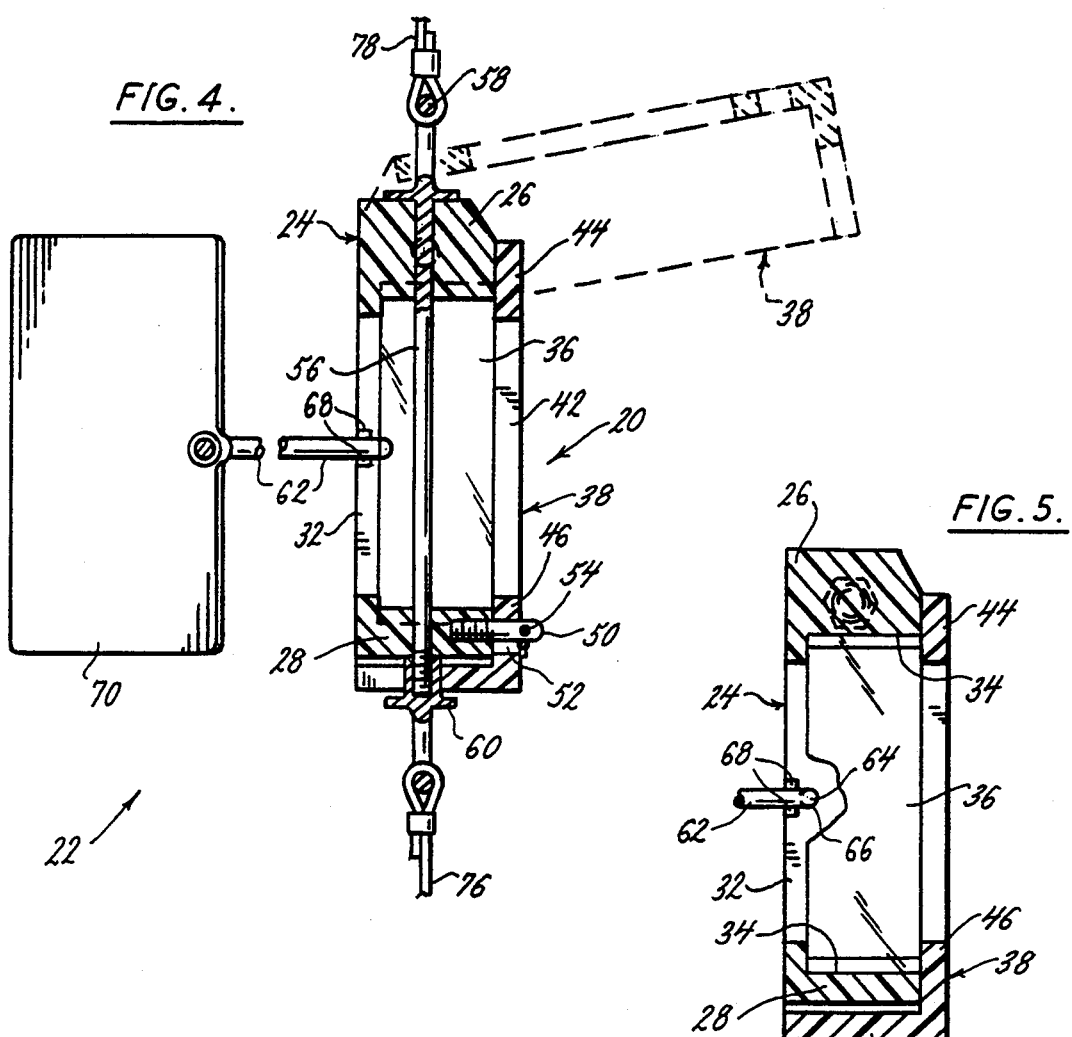
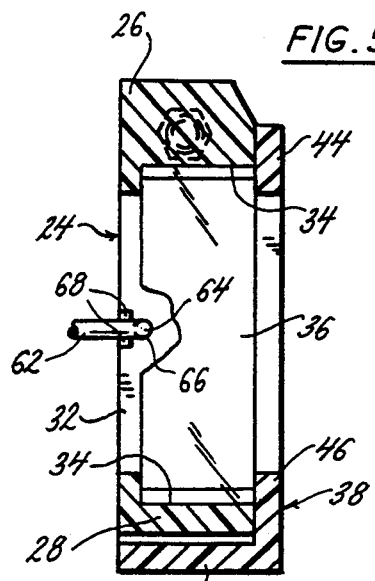
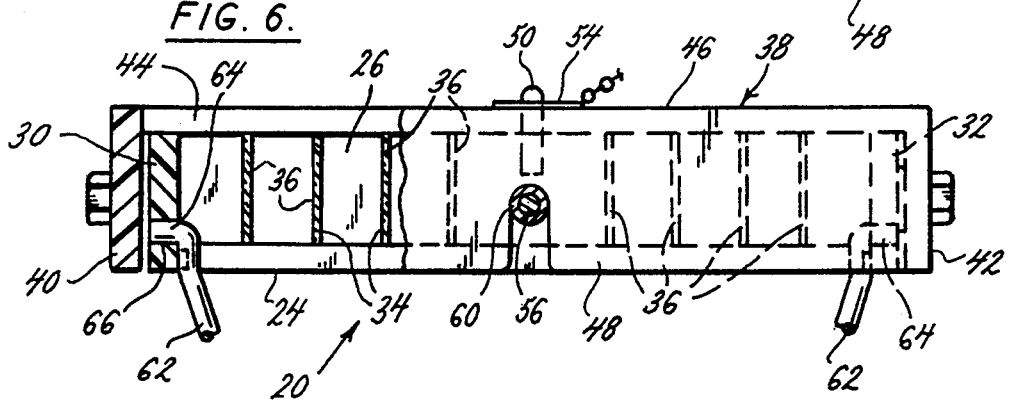
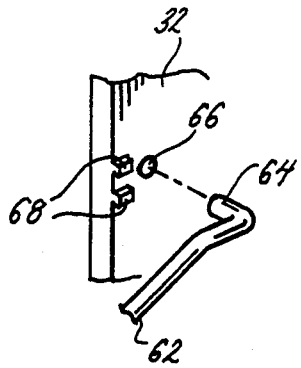

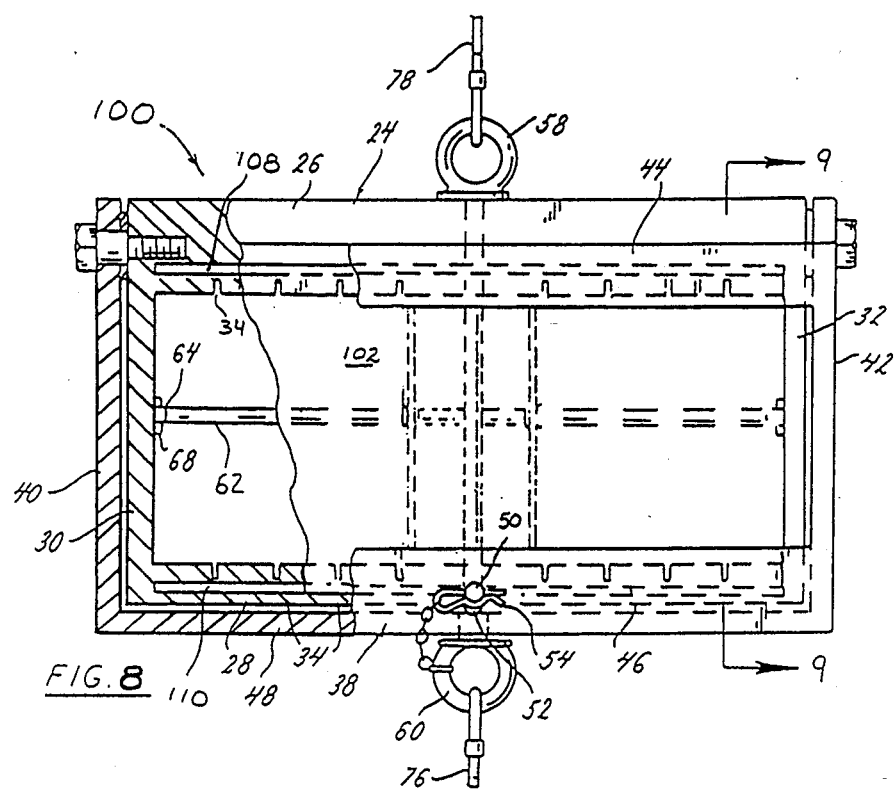
FIG. 8
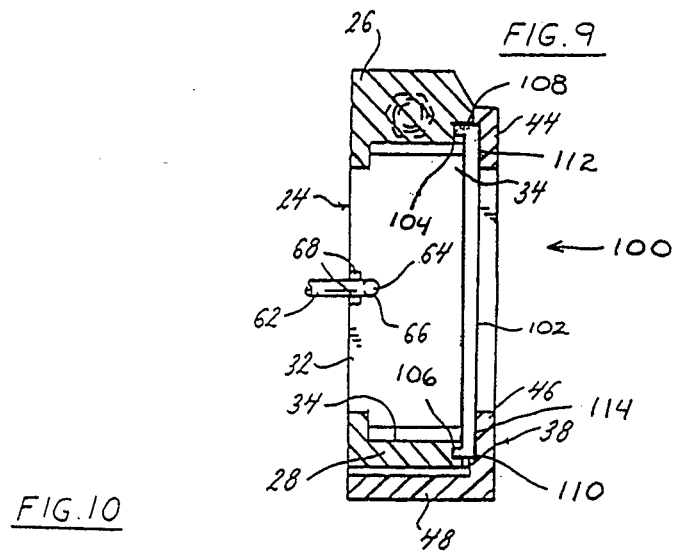
FIG. 9
FIG. 10
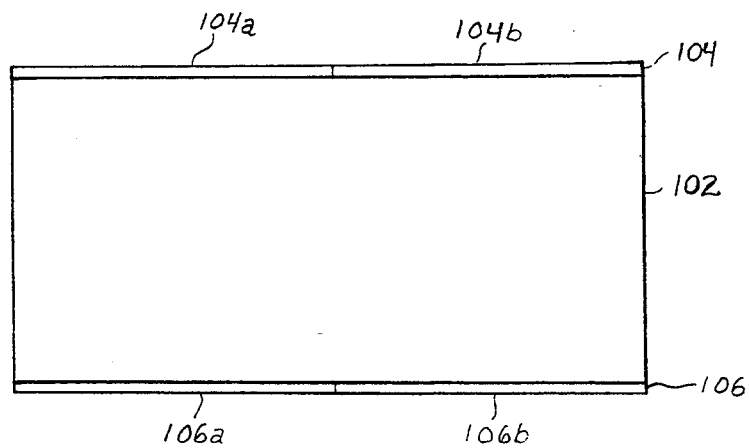

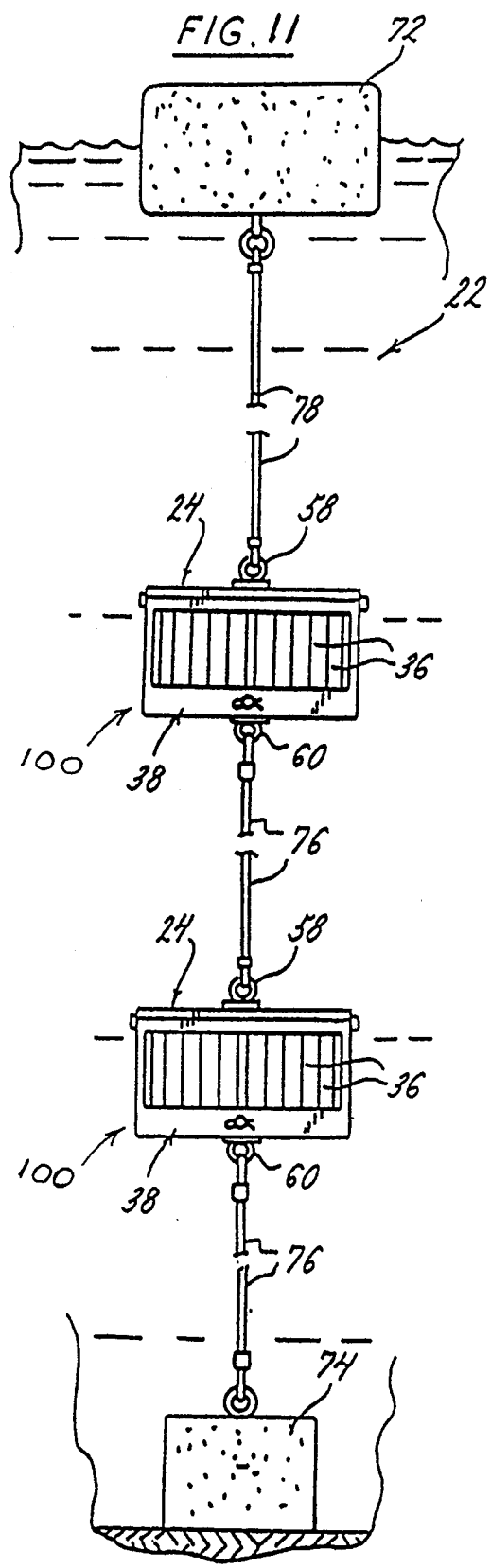

SAMPLER FOR HOLDING SLIDES AND POLYMER SCRIMS OR PADS

CROSS REFERENCE TO RELATED APPLICATION

This application is a continuation-in-part of application Ser. No. 07/759,411, filed Sep. 13, 1991 and now U.S. Pat. No. 5,219,390.

BACKGROUND OF THE INVENTION

This invention relates generally to sample collectors, and in particular to a device for collecting animal and plant samples from water.

In most bodies of water such as rivers, streams, and lakes there is a wide variety of microscopic plants and animals in the water. In evaluating the health of a body of water, it is desirable to take samples of these microscopic plants and animals. For example, in assessing whether a body of water has been infested with zebra mussels, *Dreissena polymorpha*, a biologist takes samples of the microscopic community of the water to check for the presence of veligers and post-veligers, immature stages of the zebra mussel approximately 60 to 200 microns, whose presence indicates zebra mussel infestation. A preferred method of taking samples of post-veligers is to suspend glass slides in the water for a sufficient time for the plants and animals present to adhere to the slides. One side of the slide can then be cleaned, and the slide can be examined under a microscope to determine not only the types of plants and animals present, but their relative populations. While this procedure seems straight forward, there are difficulties in suspending the slides in the water. The slides should be held in a generally upright position, the surfaces generally parallel to the flow of water. The slides must be held securely and free from obstructions that would interfere with the deposit of plants and animals. Moreover, the slides must be secure whether the water is still or flowing. It is also important to be able to support the slides at various depths in the water column.

Another preferred method of taking samples of post-veligers, as well as veligers, is to suspend a polymer scrim or pad of polymer fibers in the water for a sufficient time for the plants and animals present to collect on or in the scrim or pad. The scrim or pad can be washed to remove any animals and plants that have collected in and on the fibers, and plants and animals that are removed can be examined under a microscope to determine not only the types of plants and animals collected, but their relative populations. While this procedure seems straight forward, there are difficulties in suspending the scrim or pad in the water. Like the slides, the scrim or pad should be held in a generally upright position, however the scrim or pad should extend transversely to the water flow, so that the water flows through the scrim or pad. The scrim or pad must be held securely and free from obstructions that would interfere with the flow of water over and through the scrim or pad, and the deposit of plants and animals thereon. Moreover, the scrim or pad must be secure whether the water is still or flowing. It is also important to be able to support the scrims or pads at various depths in the water column.

Slides are primarily effective for post-veligers, and provide quantitative data. A polymer scrim is effective for both veligers and post-veligers, but primarily provides qualitative data.

Generally, the sampler devices available are designed for the collection of periphyton. See, for example the sampler device shown in Doernberg et al., U.S. Pat. No. 3,955,421. These devices are submerged near the surface of the water, and hold a plurality of vertically oriented slides in a generally horizontal plane. These devices are not adapted for, and are generally unsuitable for, holding slides in the proper vertical orientation, parallel to the flow of the water, so that the water can flow unobstructed between the slides. Moreover, these device are generally too flimsy to support the slide at any appreciable depth below the surface, as is necessary for an accurate survey of certain plants and animals such as the zebra mussel. The currently available sampler devices tend to break apart and/or lose their slides under such conditions. Moreover, installing and removing the slides from such devices is difficult.

SUMMARY OF THE INVENTION

The sampler device of the first embodiment of the present invention is adapted to securely hold slides in the correct orientation and position in a body of water. Generally, the sampler device comprises a frame having a top member, a bottom member, and left and right side members. The top and bottom members each have a plurality of vertically aligned slots therein for receiving and holding the edges of a plurality of standard glass slides. A guard is pivotally mounted to the frame, and movable between a closed position, in which portions of the guard overlap the ends of the slots in the top and bottom members of the frame, thereby securing the slides in the frame, and an open position in which the guard does not overlap the ends of the slots so that slides can be inserted into and removed from the slots. The sampler device also includes means for releasably locking the guard in its closed position. A mounting bolt extends through the top and bottom members of the frame, and attaching means associated with the bolt, are positioned above and below the frame for attaching lines to the mounting bolt.

In the preferred embodiment, the guard member comprises left and right side members, pivotally attached to the left and right sides of the frame, generally adjacent the top of the frame. Upper and lower transverse members extend between the left and right side members, in position to overlap the slots when the guard is in the closed position.

The sampler device of the second embodiment of the present invention is not only adapted to securely hold slides in the correct orientation and position in a body of water as the sampler device of the first embodiment, but the device of the second embodiment is also adapted to securely hold a collection scrim or pad in the correct orientation and position in a body of water. Generally, the sampler device of the second embodiment comprises a frame having a top member, a bottom member, and left and right side members. The top and bottom members each have a plurality of vertically aligned slots therein for receiving and holding the edges of a plurality of standard glass slides. A guard is pivotally mounted to the frame, and movable between a closed position, in which portions of the guard overlap the ends of the slots in the top and bottom members of the frame, thereby securing the slides in the frame, and an open position in which the guard does not overlap the ends of the slots so that slides can be inserted into and removed from the slots. The frame and the guard are configured to sandwich a scrim or pad between them. The sampler device also includes means for releasably locking the guard in its closed position. A mounting bolt extends through the top and bottom members of the frame, and attaching means associated with the bolt, are positioned above and below the frame for attaching lines to the mounting bolt.

In the preferred embodiment, the scrim or pad has ribs secured on the edges, and the frame has grooves therein for receiving the mounting ribs on the scrim or pad to secure the scrim or pad in the device so that the pad cannot pull free from its engagement between the frame and the guard member. The grooves preferably extend generally horizontally across the frame and the guard member comprises upper and lower transverse members positioned to overlap the grooves when the guard is in the closed position.

Like the sampler device of the first embodiment, the sampler device of the second embodiment may include vanes extending from the frame to keep the frame oriented generally perpendicular to the flow of water, thereby orienting the scrim or pad generally perpendicular to the flow. A bracket is preferably mounted between the sides of the frame, and extends generally rearwardly from the frame. Vanes are mounted on the bracket. Holes can be provided on the inside of the sides of the frames for receiving the ends of the bracket. Bosses can be provided adjacent these holes to engage the bracket and secure it against rotation relative to the frame, or grooves can be provided to secure the bracket.

The sampler devices of this invention are preferably used as part of a sampler assembly. The upper attachment means on the bolt is preferably connected to a float, and the lower attachment means on the bolt is preferably connected to a weight, so that the sampler devices can be suspended in the water column at a preselected depth between the weight and the float, at a relatively constant level.

The sampler devices of this invention are of simple yet sturdy construction. They are extremely easy to operate, and are less prone to in-service failure. The forces of suspending the sampler devices are borne by the mounting bolts, rather than the frame, so these forces do not act to pull the frame apart. Thus, the risk of the loss of valuable data and time is reduced. The devices are reusable, and require little or no maintenance. The device of the second embodiment is adaptable for use with slides for collecting quantitative data on post-veligers, and with polymer scrims for collecting qualitative data on veligers and post-veligers. These and other features and advantages will be in part apparent and in part pointed out hereinafter.

BRIEF DESCRIPTION OF THE DRAWINGS

FIG. 1 is a side elevation view of a first embodiment of a sampler assembly including a sampler device constructed according to the principles of this invention;

FIG. 2 is a horizontal cross sectional view of the sampler assembly shown in FIG. 1, showing the top of the sampler device;

FIG. 3 is an enlarged front elevation view of the sampler device of the first embodiment;

FIG. 4 is a vertical cross sectional view of the sampler device of the first embodiment taken along the plane of line 4—4 in FIG. 3;

FIG. 5 is a vertical cross sectional view of the sampler device of the first embodiment taken along the plane of line 5—5 in FIG. 3;

FIG. 6 is a horizontal cross sectional view of the sampler device of the first embodiment taken along line 6—6 in FIG. 3;

FIG. 7 is a partial perspective view of the sampler device of the first embodiment showing the attachment between the bracket and the side of the frame;

FIG. 8 is a front elevation view of a second embodiment of a sampler device constructed according to the principles of this invention;

FIG. 9 is a vertical cross-sectional view of the sampler device of the second embodiment, taken along the plane of line 9—9 in FIG. 8;

FIG. 10 is a bottom plan view of a collection pad adapted for use with the sampler device of the second embodiment; and FIG. 11 is a side elevation view of a sample assembly including two sampler devices constructed according to the principles of this invention.

Corresponding reference numerals indicate corresponding parts throughout the several views of the drawings.

DETAILED DESCRIPTION OF THE PREFERRED EMBODIMENTS

A first embodiment of a sampler device constructed according to the principles of this invention, indicated generally as 20, is shown in FIG. 1 as it would be used as part of a sampler assembly 22. The sampler device 20 comprises a frame 24. The frame 24 is a hollow rectangle having a top 26, a bottom 28, and left and right sides 30 and 32. There are a plurality of vertically aligned slots 34 in the top 26 and bottom 28, extending rearwardly from the front face of the frame. The slots 34 are generally parallel to the sides of the frame and are adapted for receiving and holding the edges of a plurality of slides 36, so that the slides are held vertically, in planes generally perpendicular to the plane of the frame 24. The slots 34 do not extend all the way to the back of the frame so that slides 36 in the slots cannot slide out the back of the frame. The slots 34 are preferably spaced so that the slides are equally spaced from each other. Thus the water flow between the slides is equal, and the chances for plant and animal deposition on each side of the slide is approximately equal. The slides 36 are preferably standard-sized glass slides, but they could be made from plastic or other suitable material. There are preferably numbers on the frame corresponding to the slots, so that positions of the slides in the sampler device can be conveniently referenced.

A guard 38 is pivotally mounted to the frame 24, and is movable between a closed position and an open position. As shown in the Figures, the guard 38 comprises left and right side members 40 and 42, which are pivotally mounted to the left and right sides of the frame 24, generally adjacent the top of the frame, for example with bolts 43. The guard 38 also comprises upper and lower transverse members 44 and 46, which extend between the left and right side members 40 and 42 of the guard. The upper transverse member 44 is positioned so that when the guard 38 is in its closed position, the upper transverse member overlaps the ends of the slots in the top 26 of the frame 24. The lower transverse member 46 is positioned so that when the guard 38 is in its closed position, the lower transverse member overlaps the ends of the slots in the bottom 28 of the frame 24. Thus, when the guard is in its closed position, any slides 36 in the slots 34 are held in place in the frame 24. The frame 24 is open, and the upper and lower transverse members are spaced sufficiently so that unlike prior sampler devices water can flow freely through the sampler device. The guard 38 may also include a bottom member 48 extending between the side members 40 and 42.

The frame 24 and the guard 38 are preferably made from a strong, tough, durable plastic such as polyvinylchloride or polycarbonate, or some other suitable material. The frame 24 and the guard 38 can be assembled from a plurality of separate pieces secured, for example, with adhesive, but preferably the frame and the guard are each one molded piece.

The sampler device 20 includes means for releasably locking the guard 38 in its closed position. This locking means can comprise a post 50 projecting from the bottom of the frame 24, and extending through an opening 52 in the guard 38 (preferably in the lower transverse member 46). Some means, such as a hitch pin 54 can be releasably secured over the end of the post 50 to prevent the guard from being moved from its closed position. The post 50 preferably has a diametrical bore for allowing the hitch pin 54 to be secured to the end of the post. A chain 55 can secure the pin 54 so that it cannot be lost.

A mounting bolt 56 extends through the top 26 and bottom 28 of the frame 24. There is an attaching means at each end of the bolt, above and below the frame. As shown in the Figures, the attaching means preferably comprises loops or eyes 58 and 60, respectively. The eyes 58 and 60 are connected to the bolt 56, but not to the frame, so that loads on the eyes, for example in anchoring the sampler device 20, are not transferred to the frame. The eye 58 can be formed integrally at one end of the bolt 56. The eye 60 is preferably threaded onto the other end of the bolt 56. The eyes 58 and 60 permit the frame to be suspended in the water vertically, so that water can flow freely through the frame.

The eyes 58 and 60 preferably pivot with respect to the frame 24, so that the frame can pivot freely in the water. Either the eyes 58 and 60 can be made to pivot freely with respect to bolt 56, or the eyes 58 and 60 and the bolt 56 can be made to pivot with respect to the frame 24.

The sampler device 20 preferably also includes a vane for keeping the frame of the sampler device oriented perpendicular to the currents in the water. A three-sided wire bracket 62 extends rearwardly from the frame 24. As shown in FIG. 7, the ends 64 of the bracket 62 are adapted to fit into openings 66 on the inside of the sides 30 and 32 of the frame. Bosses 68 adjacent the openings 66, engage the bracket 62, and prevent it from pivoting relative to the frame. The resilience of the bracket holds the ends between the sides. Alternatively, the ends of the bracket can be adapted to fit in openings on the outside of sides 30 and 32 of the frame 24. Thus, when the guard 38 is closed over the frame, the guard holds the ends of the bracket in place, preventing the bracket from being dislodged. Grooves can be provided in the outside of sides 30 and 32 to accommodate the bracket, and hold it generally horizontally with respect to the frame.

Vanes 70 extend from the bracket at oblique angles with respect to the frame. The vanes 70 are positioned symmetrically with respect to the frame, so that vanes keep the frame oriented perpendicular to the water currents, thereby keeping the slides 36 in the frame parallel to the currents. Thus the bracket 62 can easily be attached to or removed from the frame 24, by simply compressing the bracket and inserting ends 64 into openings 66, or pulling ends 64 from openings 66. The bracket 62 is preferably sufficiently large so that the vanes 70 are spaced sufficiently from the frame that they do not interfere with the flow of water through the frame. As described above, the frame preferably rotates freely with respect to the eyes 58 and 60, and thus can pivot freely to the correct orientation as dictated by the vanes 70, independent of its mounting.

The sampler device 20 is adapted to be used as part of a sampler assembly 22. The sampler assembly 22 comprises at least one of the sampler devices 20, a float 72 and a weight 74. A line 76 connects the weight 74 and the eye 60 at the bottom of the frame 24. A line 78 connects the float 72 and the eye 58 at the top of the frame 24. The lines 76 and 78 can be attached to their respective eyes 58 and 60 with a rope, a carabinier, a safety snap, or, as shown in the Figures, with a loop in the line secured with a ferrule. Thus the sampler device 20 is held in a relatively constant vertical position in the water column, between the weight and the float. The position of the sampler device is determined by the length of the lines. Of course, if desired, more than one sampler 20 could be positioned in the water column. See FIG. 11. In this case a line would connect the weight to the eye 60 at the bottom of the frame of the lowermost sampler device 20, another line would connect the float to the eye 58 of at the top of the uppermost sampler device 20, and additional lines would connected the upper and lower eyes of adjacent sampler devices 20 so that each is held at a relatively constant vertical position in the water column. The weight can be relatively large, so that the position of the devices relative to the bottom is fixed. The weight can also be relatively small so that the position of the devices relative to the surface is fixed, while permitting the device to rise and fall with the surface of the water.

Alternatively, the sampler devices 20 could be deployed in some other manner, for example it is possible to suspend one sampler device 20, or a series of sampler devices 20, from a stationary anchoring point such as a railing.

A second embodiment of a sampler device constructed according to the principles of this invention, indicated generally as 100 in FIGS. 8 and 9. The sampler device 100 is similar in construction to sampler 20 of the first embodiment, and corresponding parts are identified with corresponding reference numerals. However, in addition to being adapted for mounting slides, the sampler device 100 is also adapted to mount a polymer scrim or pad 102. It has been discovered that a scrim or pad of polymer fibers makes an excellent substrate for collection plant and animal samples from water. The water flows in and around the scrim, and the plants and animals readily collect on or in the polymer fibers. The scrim or pad can comprise polyethylene, polypropylene, nylon, or other suitable fiber.

To facilitate the mounting of the scrim or pad 102, it can be provided with ribs 104 and 106 at the top and bottom edges, respectively. The ribs 104 and 106 are preferably segmented into two or more pieces 104a and 104b and 106a and 106b, respectively. This allows the scrim or pad to be folded, so that it can be conveniently fit into a collection jar or bag after use.

There is preferably a groove 108 in the top 26 of the frame 24, and a groove 110 in the bottom 28 of the frame 24. The grooves 108 and 110 are adapted to receive the ribs 104 and 106 on the pad 102 to hold the pad 102 stretched over the frame 24. The top of the frame has a recess or relieved portion 112, and the bottom of the frame has a recess or relieved portion 114, to accommodate the scrim or pad, providing sufficient clearance for the pad to pass between the frame and the guard.

The guard 38 is pivotally mounted to the frame 24, and is movable between a closed position and an open position, and when in the closed position the upper and lower transverse members 44 and 46 overlap the grooves 108 and 110, trapping the ribs 104 and 106 therein. The scrim or pad extends in the recesses 112 and 114. Thus, when the guard is in its closed position, the scrim or pad 102 is held in place on the frame 24. The frame 24 is open, and the upper and lower transverse members are spaced sufficiently so that water can flow freely through the sampler device. Thus water can flow freely through the scrim or pad 102, so that plants and animals can deposit on the scrim or pad.

The sampler device 100 is adapted to be used as part of a sampler assembly 22'. The sampler assembly 22' comprises at least one of the sampler devices 20, a float 72 and a weight 74. A line 76 connects the weight 74 and the eye 60 at the bottom of the frame 24. A line 78 connects the float 72 and the eye 58 at the top of the frame 24. The lines 76 and 78 can be attached to their respective eyes 58 and 60 with a rope, a carabinier, a safety snap, or, as shown in the Figures, with a loop in the line secured with a ferrule. Thus the sampler device 100 is held in a relatively constant vertical position in the water column, between the weight and the float. The position of the sampler device is determined by the length of the lines. Of course, if desired, more than one sampler 100 could be positioned in the water column. In this case a line would connect the weight to the eye 60 at the bottom of the frame of the lowermost sampler device 100, another line would connect the float to the eye 58 of at the top of the uppermost sampler device 100, and additional lines would connected the upper and lower eyes of adjacent sampler devices 100 so that each is held at a relatively constant vertical position in the water column. The weight can be relatively large, so that the position of the devices relative to the bottom is fixed. The weight can also be relatively small so that the position of the devices relative to the surface is fixed, while permitting the device to rise and fall with the surface of the water.

Alternatively, the sampler devices 100 could be deployed in some other manner, for example it is possible to suspend one sampler device 100, or a series of sampler devices 100, from a stationary anchoring point such as a railing.

OPERATION

In operation, with the guard 38 of the sampler device 20 open, clean glass slides 36 are installed in the slots 34 in the frame 24. When the required number of slides have been installed, the guard 38 is pivoted to its closed position. The guard is secured in its closed position by attaching hitch pin 54 to the end of the post 50, which prevents the guard 38 from being lifted from its closed position. The eye 60 is connected by a line 76 to the weight 74, and the eye 58 is connected by a line 78 to the float. The weight is then allowed to sink in the water column, which holds the sampler device under water, at a preselected level determined by the length of the line 76. The vanes 70 keep the frame oriented perpendicular to the flow of currents, so that water flows freely through the frame between the slides.

After the sampler device 20 has been immersed for the desired amount of time (typically about one to four weeks for a zebra mussel survey), the sampler device is removed from the water. The hitch pin 54 is removed from the post 50, the guard 38 is lifted, and the slides are removed from their slots, whereupon they can be examined. The sampler device can be cleaned, if necessary, and it is ready for reuse.

In operation, with the guard 38 of the sampler device 100 open, a clean scrim or pad 102 is mounted on the frame, with the ribs 104 and 106 in the grooves 108 and 110. When the scrim or pad 102 is in place, the guard 38 is pivoted to its closed position. The guard is secured in its closed position by attaching hitch pin 54 to the end of the post 50, which prevents the guard 38 from being lifted from its closed position. The eye 60 is connected by a line 76 to the weight 74, and the eye 58 is connected by a line 78 to the float. The weight is then allowed to sink in the water column, which holds the sampler device under water, at a preselected level determined by the length of the line 76. The vanes 70 keep the frame oriented perpendicular to the flow of currents, so that water flows freely through the frame and through the scrim or pad 102.

After the sampler device 100 has been immersed for the desired amount of time (typically about 24–72 hours for a zebra mussel survey), the sampler device is removed from the water. The hitch pin 54 is removed from the post 50, the guard 38 is lifted, and the pad 102 is removed. Because of the segmented construction of the ribs 104 and 106, the pad 102 can be folded and placed in a bag or jar for storage until it can be examined. The sampler device 100 can be cleaned, if necessary, and it is ready for reuse.

As various changes could be made in the above constructions without departing from the scope of the invention, it is intended that all matter contained in the above description or shown in the accompanying drawings shall be interpreted as illustrative and not in a limiting sense.

What is claimed is:

1. A sampler device for supporting a polymer scrim or pad under water for the collection of plant and animal samples, the device comprising:
   a frame having a top member, a bottom member, and left and right side members, the top and bottom members having a recess therein for engaging the edges of the polymer scrim or pad;
   a guard pivotally mounted to the frame, and movable between a closed position, in which portions of the guard overlap the grooves in the top and bottom members of the frame, thereby securing the scrim or pad in the frame, and an open position in which the guard does not overlap the grooves so that scrim or pad can be inserted into and removed from the grooves;
   means for releasably locking the guard in its closed position;
   a mounting bolt extending through the top and bottom of the frame, and attaching means associated with the bolt above and below the frame for securing the sampler device.

2. The sampler device according to claim 1 wherein the recess in the top and bottom members of the frame includes a horizontally extending groove.

3. The sampler device according to claim 2 further comprising a polymer scrim or pad having an upper mounting rib generally adjacent the upper edge of the scrim or pad, and a lower mounting rib generally adjacent the lower edge of scrim or pad, the scrim or pad being mounted on the frame with the upper mounting rib received in the groove in the upper frame member, and the lower rib being received in the groove in the lower frame member.

4. The sampler device according to claim 3 wherein the upper mounting rib and the lower mounting rib are segmented, to permit the scrim or pad to be folded perpendicular to the ribs.

5. The sampler device according to claim 1 wherein the guard member comprises left and right side members, pivotally attached to the left and right sides of the frame, and upper and lower transverse members extending between the left and right side members, the transverse members adapted to overlap the grooves when the guard is in the closed position.

6. The sampler device according to claim 1 wherein the means for locking the guard in its closed position comprises a post extending from the frame through an opening in the guard, and means attachable to the end of the post to prevent the guard from being removed from the post.

7. The sampler device according to claim 6 wherein a bracket is mounted between the sides of the frame, and wherein the vanes are mounted on the bracket.

8. The sampler device according to claim 7 further comprising means on the sides of the frame to secure the bracket against rotation relative to the frame.

9. The sampler device according to claim 1 further comprising vanes extending from the frame to keep the frame oriented generally perpendicular to the flow of the water in which it is immersed.

10. A sampler assembly comprising at least one of the sampler devices as set forth in claim 1, a weight, a float, and a first line connecting the float and the attaching means at the top of the frame, and a second line connecting the weight and the attaching means at the bottom of the frame, so that the sampler device is held at a relatively constant level in the water between the weight and the float.

11. A sampler assembly comprising a plurality of the sampler devices as set forth in claim 1, a weight, a float, and a line connecting the float and the attaching means at the top of the frame of one of the sampler devices, a line connecting the weight and the attaching means at the bottom of another of the sampler devices, and lines connecting the upper and lower attaching means of the other sampler devices so that each sampler device is held at a relative constant level in the water between the weight and the float.

12. A sampler device adapted for supporting glass slides and/or a polymer scrim or pad under water for the collection of plant and animal samples, the device comprising:

a frame having a top member, a bottom member, and left and right side members, the top and bottom members having a plurality of vertically aligned slots therein for receiving and holding the edges of a plurality of glass slides, and further having horizontally extending groove therein for engaging the edges of the polymer scrim or pad;

a guard pivotally mounted to the frame, and movable between a closed position, in which portions of the guard overlap the ends of the slots in the top and bottom members of the frame to secure any slides in the slots, and in which portions of the guard also overlap the grooves in the top and bottom members of the frame to secure any scrim or pad mounted in the grooves in the frame, and an open position in which the guard does not overlap the slots or the grooves so that slides can be inserted into and removed from the slots and a scrim or pad can be inserted into and removed from the grooves;

means for releasably locking the guard in its closed position;

a mounting bolt extending through the top and bottom of the frame, and attaching means associated with the bolt above and below the frame for securing the sampler device.

* * * * *